(12) United States Patent
Sherman

(10) Patent No.: US 7,070,594 B2
(45) Date of Patent: Jul. 4, 2006

(54) SYSTEM AND METHOD FOR ASSESSING ICE BALL FORMATION DURING A CRYOABLATION PROCEDURE

(75) Inventor: Marshall Sherman, Cardiff by the Sea, CA (US)

(73) Assignee: CryoCor, Inc., San Diego, CA (US)

(*) Notice: Subject to any disclaimer, the term of this patent is extended or adjusted under 35 U.S.C. 154(b) by 103 days.

(21) Appl. No.: 10/775,277

(22) Filed: Feb. 10, 2004

(65) Prior Publication Data

US 2005/0177146 A1    Aug. 11, 2005

(51) Int. Cl.
*A61B 18/18* (2006.01)

(52) U.S. Cl. .............. 606/21; 606/20; 606/22; 606/23; 600/547

(58) Field of Classification Search ............ 606/21, 606/20, 22, 23; 600/547
See application file for complete search history.

(56) References Cited

U.S. PATENT DOCUMENTS

| | | | |
|---|---|---|---|
| 3,696,813 A | 10/1972 | Wallach | |
| 3,913,581 A | 10/1975 | Ritson et al. | |
| 4,018,227 A | 4/1977 | Wallach | |
| 5,053,033 A | 10/1991 | Clarke | |
| 5,069,223 A * | 12/1991 | McRae ............... | 600/547 |
| 5,139,496 A | 8/1992 | Hed | |
| 5,147,355 A | 9/1992 | Friedman et al. | |
| 5,281,213 A | 1/1994 | Milder et al. | |
| 5,281,215 A | 1/1994 | Milder | |
| 5,423,807 A | 6/1995 | Milder | |
| 5,759,182 A | 6/1998 | Varney et al. | |
| 5,869,971 A | 2/1999 | Sherman | |
| 5,876,399 A | 3/1999 | Chia et al. | |
| 5,899,898 A | 5/1999 | Arless et al. | |
| 5,899,899 A | 5/1999 | Arless et al. | |
| 5,992,158 A | 11/1999 | Goddard et al. | |
| 6,024,740 A | 2/2000 | Lesh et al. | |
| 6,048,919 A | 4/2000 | McCullough | |
| 6,117,101 A | 9/2000 | Diederich et al. | |
| 6,139,544 A | 10/2000 | Mikus et al. | |
| 6,190,378 B1 * | 2/2001 | Jarvinen ............... | 606/21 |
| 6,235,018 B1 * | 5/2001 | LePivert ............... | 606/20 |
| 6,235,019 B1 | 5/2001 | Lehmann et al. | |
| 6,237,355 B1 | 5/2001 | Li | |
| 6,245,064 B1 | 6/2001 | Lesh et al. | |
| 6,251,105 B1 | 6/2001 | Mikus et al. | |
| 6,280,439 B1 | 8/2001 | Martin et al. | |
| 6,283,959 B1 | 9/2001 | Lalonde et al. | |
| 6,383,180 B1 | 5/2002 | Lalonde et al. | |
| 6,391,024 B1 * | 5/2002 | Sun et al. ............... | 606/34 |

(Continued)

*Primary Examiner*—Michael Peffley
*Assistant Examiner*—Alex Toy
(74) *Attorney, Agent, or Firm*—Nydegger & Associates

(57) ABSTRACT

Systems and methods for assessing the formation of an ice ball during a cryoablation procedure are disclosed. The system includes a reference electrode that is placed in contact with the patient and a cryocatheter having a cryotip. An electronic circuit is connected to both the cryotip and the reference electrode to measure the impedance therebetween which can be used to assess the formation of an ice ball during a cryoablation procedure. An exemplary measurement signal has a frequency of approximately 20 khz and an RMS voltage of approximately 0.5V. With the cryotip positioned proximate the target tissue, a reference impedance is measured. Next, the conductive tip member is placed in contact with the target tissue and cooled to form an ice ball. During cooling, impedance measurement(s) are taken and compared with the reference impedance to assess the formation of the ice ball.

17 Claims, 4 Drawing Sheets

U.S. PATENT DOCUMENTS

| | | |
|---|---|---|
| 6,407,149 B1 | 6/2002 | McCullough |
| 6,468,268 B1 | 10/2002 | Abboud et al. |
| 6,471,693 B1 * | 10/2002 | Carroll et al. ............... 606/21 |
| 6,527,769 B1 | 3/2003 | Langberg et al. |
| 6,540,740 B1 | 4/2003 | Lehmann et al. |
| 6,551,309 B1 * | 4/2003 | LePivert .................... 606/20 |
| 6,562,030 B1 | 5/2003 | Abboud et al. |
| 6,569,158 B1 | 5/2003 | Abboud et al. |
| 6,575,966 B1 | 6/2003 | Lane et al. |
| 6,579,287 B1 | 6/2003 | Wittenberger et al. |
| 6,585,728 B1 | 7/2003 | Heiner et al. |
| 6,585,729 B1 | 7/2003 | Eum |
| 6,589,234 B1 | 7/2003 | Lalonde et al. |
| 6,592,577 B1 | 7/2003 | Abboud et al. |
| 6,595,988 B1 | 7/2003 | Wittenberger et al. |
| 6,602,247 B1 | 8/2003 | Lalonde |
| 6,605,087 B1 | 8/2003 | Swartz et al. |
| 6,629,972 B1 | 10/2003 | Lehmann et al. |
| 6,635,053 B1 | 10/2003 | Lalonde et al. |
| 6,733,494 B1 | 5/2004 | Abboud et al. |
| 6,755,823 B1 | 6/2004 | Lalonde |
| 6,761,714 B1 | 7/2004 | Abboud et al. |
| 2001/0021847 A1 | 9/2001 | Abboud et al. |
| 2001/0025075 A1 | 9/2001 | Smith et al. |
| 2002/0025998 A1 | 2/2002 | McCullough et al. |
| 2002/0062122 A1 | 5/2002 | Lehmann et al. |
| 2002/0111612 A1 | 8/2002 | Lalonde et al. |
| 2002/0115989 A1 | 8/2002 | Abboud et al. |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0097124 A1 | 5/2003 | Lehmann et al. |
| 2004/0049178 A1 | 3/2004 | Abboud et al. |
| 2004/0054361 A1 | 3/2004 | Lehmann et al. |
| 2005/0038422 A1 * | 2/2005 | Maurice ..................... 606/21 |

* cited by examiner

SYSTEM AND METHOD FOR ASSESSING ICE BALL FORMATION DURING A CRYOABLATION PROCEDURE

FIELD OF THE INVENTION

The present invention pertains generally to surgical instruments. More particularly, the present invention pertains to systems and methods for cryoablating internal target tissue. The present invention is particularly, but not exclusively, useful for assessing the formation of an ice ball that is formed during a cryoablation procedure.

BACKGROUND OF THE INVENTION

As the word itself implies, "cryoablation" involves the ablation of tissue (i.e. tissue necrosis or destruction) using extremely low (i.e. cryogenic) temperatures. Typically, cryoablation requires lowering the temperature of the tissue to below approximately minus twenty degrees Centigrade (−20° C.). However, more efficient ablation procedures often call for temperatures as low as minus eighty eight degrees Centigrade (−88° C.) or lower. At these low temperatures, portions of the tissue and surrounding body fluids (e.g. blood), which would otherwise be in a liquid state, freeze and become solid. The result is commonly referred to as an "ice ball."

It is often desirable to cryoablate internal tissue in a relatively non-invasive procedure. For this purpose, cryocatheters have been developed, such as the cryocatheter and associated refrigeration system that is disclosed in co-pending U.S. patent application Ser. No. 10/243,997, entitled "A Refrigeration Source for a Cryoablation Catheter." Co-pending U.S. application Ser. No. 10/243,997 was filed on Sep. 12, 2002, is assigned to the same assignee as the present invention, and is hereby incorporated by reference herein. In one exemplary application of a cryocatheter, conduction blocks can be created that are particularly effective for curing heart arrhythmias, such as atrial fibrillation.

In a typical cryocatheter procedure, the distal portion (i.e. cryotip) of the catheter is positioned near or in contact with the tissue requiring ablation (i.e. the target tissue). Next, the cryotip is cooled to a cryogenic temperature to thereby cool and ablate the target tissue. During cooling of the cryotip, an ice ball forms and grows. Eventually, the entire tip becomes covered with ice and the size of the ice ball stabilizes. In a typical procedure, the stable ice ball is maintained for a predetermined residence time (e.g. 5 minutes) to achieve an effective tissue ablation.

With the above in mind, it would be desirable to assess and monitor the formation of the ice ball for several reasons. For one, the formation of an ice ball provides an indication that the cryotip is correctly positioned relative to the tissue. In the case where the cryotip is improperly positioned (e.g. when the cryotip is still fully immersed in the bloodstream) an ice ball will not usually form. In addition, monitoring the time at which the size of the ice ball stabilizes facilitates the application of an accurate and consistent ice ball residence time. This results in an effective cryoablation with minimal complications.

In light of the above, it is an object of the present invention to provide systems and methods suitable for the purposes of assessing the formation of an ice ball during a cryoablation procedure. It is another object of the present invention to provide systems and methods for assessing the formation of an ice ball using measurement signals that do not adversely affect the electrical function of the heart. It is yet another object of the present invention to provide systems and methods for assessing an ice ball which are easy to use, relatively simple to implement, and comparatively cost effective.

SUMMARY OF THE PREFERRED EMBODIMENTS

The present invention is directed to systems and methods for assessing the formation of an ice ball during a cryoablation procedure. The system includes a reference electrode, such as a backplate, that is placed in contact with the patient at the beginning of the procedure. For the present invention, the system further includes a cryocatheter having a cryotip. In a typical embodiment, the cryotip includes a thermally conductive tip member that is formed with an expansion chamber. The cryocatheter can further include a supply tube for delivering a refrigerant to the expansion chamber from a refrigerant supply unit that is located extracorporeally. For this embodiment, expansion of the refrigerant in the chamber is used to cool the tip member.

For the system of the present invention, an electronic circuit is connected to both the conductive tip member and the reference electrode. For this connection, the electronic circuit is configured to generate a measurement signal having a known voltage. The measurement signal is then used to determine the impedance between the conductive tip member and the reference electrode. Specifically, an ammeter is used to measure the current between the conductive tip member and the reference electrode, and the measured current can then be converted to an impedance. This impedance, in turn, can then be used to assess the formation of an ice ball during a cryoablation procedure. In a preferred implementation, a measurement signal having a frequency of approximately 20 khz and an RMS voltage of approximately 0.5V is used to measure the current between the conductive tip member and the reference electrode. With this frequency and voltage, the heart is not adversely stimulated by the measurement signal.

In one aspect of the present invention, the electronic circuit produces the measurement signal by first generating a square wave. Next, a four pole, low pass, active filter is used to convert the square wave to a sine wave. The sine wave is then rectified using a plurality of analog switches that are driven by a 20 khz signal that is phase shifted relative to the sine wave by approximately 90 degrees.

In a typical operation, the cryotip is inserted into the vasculature of the patient and advanced until it is positioned at a location that is proximate to the target tissue. Next, a reference impedance between the cryotip and the reference electrode is measured. Generally, at this point, the cryotip is fully immersed in a flowing blood stream and, as a consequence, the reference impedance is relatively low. Next, the conductive tip member is manipulated into contact with the target tissue. Because the impedance of the tissue is about 20 to 30 percent higher than the blood pool, the electrical current flowing between the cryotip and the reference electrode will decrease.

With the tip member in contact with the target tissue, refrigerant is then expanded in the chamber to cool the tip member. This cooling creates an ice ball and cryoablates the target tissue. Specifically, the ice ball will typically include frozen portions of blood and tissue. During formation of the ice ball, one or more assessment impedance measurements (between the cryotip and the reference electrode) are performed. As the ice ball grows, the measured impedance between the tip member and the reference electrode increases. Specifically, the conductance is proportional to the area of the tip member that is not in contact with the ice ball. When the entire tip member is covered with ice, the impedance becomes relatively high and stabilizes (i.e. current flow reduces to almost zero and stabilizes). In a typical procedure, the impedance is monitored until the entire tip member is covered with ice, and thereafter, cooling is controlled to maintain the ice ball for a predetermined time period (e.g. five minutes) to effectively cryoablate the target tissue.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
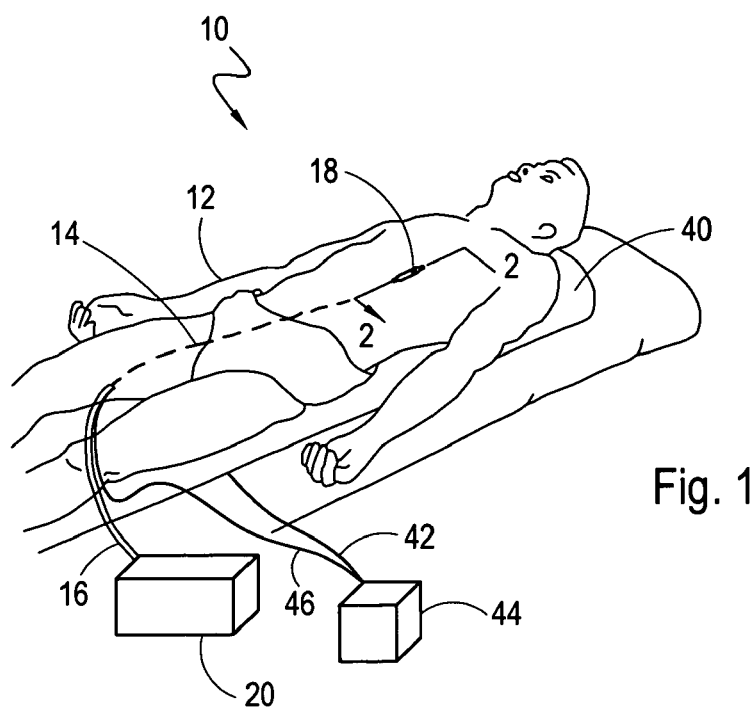
FIG. 1 is a perspective view of a system for cryoablating internal target tissue shown operationally positioned in a patient.

Referring initially to FIG. 1, a system 10 for ablating internal target tissue of a patient 12 is shown. As shown, the system 10 includes a catheter 14 that extends from a proximal end 16 that remains outside the patient's body during the procedure to a distal end 18 that can be inserted into a vasculature. From FIG. 1 it can be seen that the distal end 18 of the catheter 14 has been inserted into the vasculature of patient 12 through an artery such as the femoral artery, and then advanced through the patient's vasculature until the distal end 18 is positioned in the upper body of the patient 12. FIG. 1 further shows that the proximal end 16 of the catheter 14 is connected to a fluid refrigerant supply unit 20.

Figure 2:
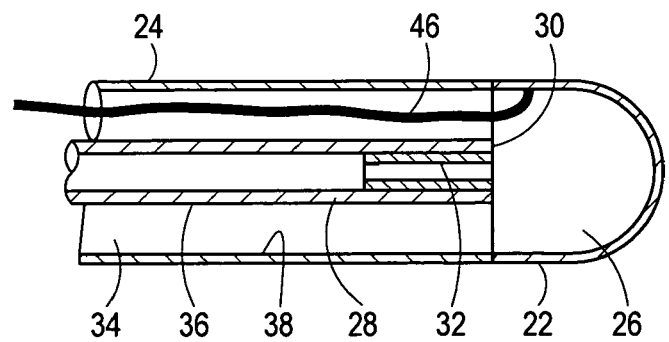
FIG. 2 is cross sectional view of a distal portion of the cryoablation system as seen along line 2—2 in FIG. 1.

Referring now to FIG. 2, the cryotip (i.e. the distal portion) of the catheter 14 is shown in greater detail. As shown, the catheter 14 includes a tip member 22 that is attached to the distal end of a catheter tube 24. As further shown, the tip member 22 is formed with an expansion chamber 26. For the system 10, the tip member 22 is made of a thermally conductive material such as a metal. A supply tube 28 is provided having a proximal end that is connected to the refrigerant supply unit 20 (see FIG. 1) and a distal end 30. A restriction 32 can be positioned in the supply tube 28 at the distal end 30 to restrict the flow of refrigerant. It can also be seen that a refrigerant return line 34 is established between the outer surface 36 of the supply tube 28 and the inner surface 38 of the catheter tube 24.

Referring back to FIG. 1, it is shown that the system 10 includes a reference electrode, which in this case is a backplate 40, that is placed in contact with the patient 12 and electrically connected via lead wire 42 to an electronic circuit 44. Although a backplate 40 is used in the system 10 as a reference electrode, those skilled in the art will appreciate that any other type of reference electrode that can be placed in contact via an electrical pathway with the vasculature/blood pool can be used, including an electrode that is incorporated into the catheter 14. Cross-referencing FIGS. 1 and 2, it can be seen that the tip member 22 is also electrically connected to the electronic circuit 44 via lead wire 46. With this cooperation of structure, the electronic circuit 44 can be used to measure the current that passes from the tip member 22 to the backplate 40. This current is indicative of an impedance between the tip member 22 and the backplate 40. Moreover, a ratio of currents, measured using the same applied voltage, is indicative of a ratio of impedances.

Figure 3:
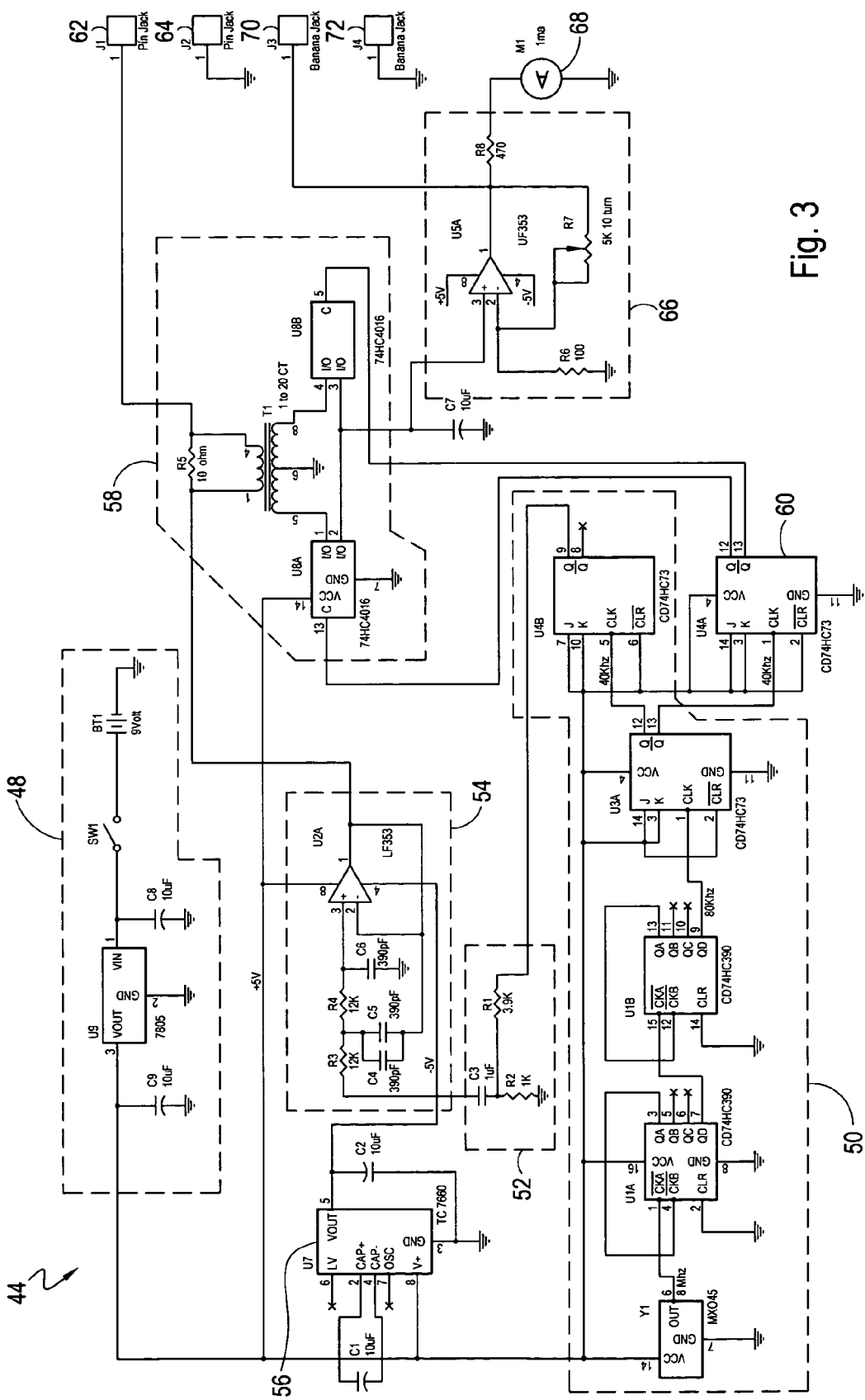
FIG. 3 is a schematic diagram of an electrical circuit for measuring a current between a cryotip and a backplate.

A better understanding of the electronic circuit 44 can be obtained with reference to FIG. 3. In overview, the electronic circuit 44 is configured to generate a measurement signal having a frequency of approximately 20 khz and an RMS voltage of approximately 0.5V. The measurement signal is then used to measure the current between the tip member 22 and the backplate 40. With this frequency and voltage, the heart is not adversely stimulated by the measurement signal. In greater structural detail, as shown in FIG. 3, the electronic circuit 44 includes a power source (box 48) having a 9V battery and a regulator which regulates the output voltage of the power source to approximately +5V. The electronic circuit 44 further includes a square wave generator (box 50) which generates an 8 Mhz square wave which is then successively reduced in frequency to 800 khz, 80 khz, 40 khz and then 20 khz by a series of CMOS chips. From the square wave generator (box 50), the signal is passed through an RC circuit (box 52) where the voltage is reduced from 5V to approximately 1V and any DC component of the signal is eliminated.

Continuing now with reference to FIG. 3, from the RC circuit (box 52), the signal is passed through a four pole, low pass, active filter (box 54) to convert the square wave to a sine wave. Specifically, harmonics having a frequency greater than 20 khz are eliminated by the four pole, low pass, active filter (box 54). A minus 5V signal is generated by circuit 56 for use by the four pole, low pass, active filter (box 54). The sine wave is then rectified (box 58) using two analog switches and a center tap transformer. As shown in FIG. 3, the switches are driven by two 20 khz signals (generated by circuit 60) that are phase shifted relative to the sine wave by approximately 90 degrees and 270 degrees, respectively. This compensates for the 90 degree phase shift that occurs as the signal passes through the four pole, low pass, active filter (box 54). From the rectification circuit (box 58), the signal is routed to a pin jack 62. In use, lead wire 46 (see FIG. 2) that is attached to tip member 22 is connected to the pin jack 62. Current returns through the backplate 40 (see FIG. 1) via lead wire 42 that is connected to pin jack 64, which is grounded.

FIG. 3 further shows that the electronic circuit 44 includes a 1:500×DC amplifier (box 66) that amplifies the signal and forwards it to an ammeter 68 where the current of the signal is measured. Banana jacks 70, 72 allow for voltage output and current logging. For some implementations, the banana jacks 70, 72 can be used to transfer the signal to an analog/digital converter and then on to a microprocessor which can then use the measured data to control other subsystems of the system 10.

Operation

Figure 4:
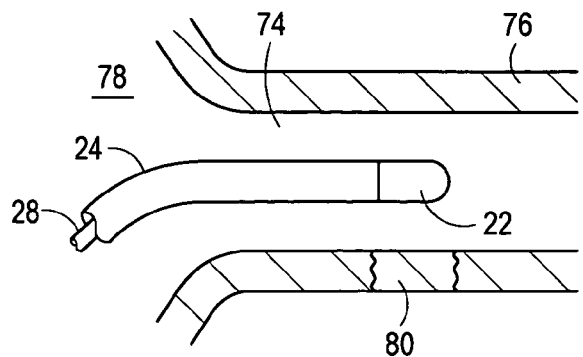
FIG. 4 is a perspective view of a distal portion of the cryoablation system shown in FIG. 1, shown positioned at a treatment site in the vasculature of a patient.
Figure 5:
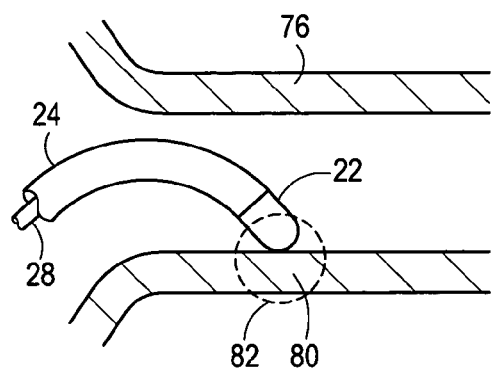
FIG. 5 is a perspective view as in FIG. 4, shown after the tip member has contacted the target tissue and been cooled to form an ice ball which covers approximately half of the tip member.
Figure 6:
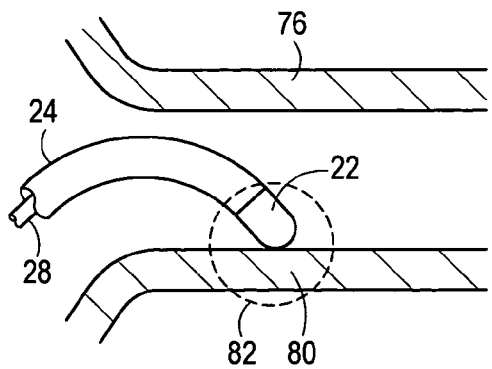
FIG. 6 is a perspective view as in FIGS. 4 and 5, shown after the tip member has contacted the target tissue and been cooled to form an ice ball which covers the entire tip member.

The operation of the system 10 can best be appreciated with reference to FIGS. 4–6 which show an exemplary treatment site near the ostium 74 of a pulmonary vein 76 where the pulmonary vein 76 connects to the left atrium 78. The catheter tube 24 can be used to advance the tip member 22 to the treatment site. At the treatment site, as shown in FIG. 4, the tip member 22 is positioned proximate the target tissue 80 to be cryoablated. Next, a reference impedance between the tip member 22 and the backplate 40 (see FIG. 1) is measured using the electronic circuit 44. At this point, the cryotip is typically immersed in a flowing blood stream, and as a consequence, the reference impedance (illustrated by point A in FIG. 7) is relatively low. Next, as shown in FIG. 5, the conductive tip member 22 is placed in contact with the target tissue 80. Because the impedance of the tissue is about 20 to 30 percent higher than the blood pool, the impedance between the tip member 22 and the backplate 40 increases (illustrated by the increase in impedance from point B to point C in FIG. 7).

With the tip member 22 in contact with the target tissue 80, a fluid refrigerant, such as Nitrous Oxide, from the refrigerant supply unit 20 (see FIG. 1) is transferred through the supply tube 28 and into the expansion chamber 26 (see FIG. 2) of the tip member 22. Inside the expansion chamber 26, the fluid undergoes an endothermic expansion to absorb heat from the tip member 22 (and target tissue 80). Typically, a fluid refrigerant is used that transitions from a liquid state to a gaseous state as it expands into the expansion chamber 26. Heat absorbed by the refrigerant during this phase transition (i.e. latent heat) cools the tip member 22, which in turn cools the target tissue 80 and portions of the blood pool in the pulmonary vein 76. After expansion, the gaseous fluid refrigerant can pass through the return line 34 (see FIG. 2) and exit the patient 12 (see FIG. 1).

As shown in FIG. 5, the cooled tip member 22 creates an ice ball 82 and cryoablates the target tissue 80. Specifically, as shown, the ice ball 82 will typically include frozen portions of blood and tissue. During formation of the ice ball 82, one or more assessment impedance measurements (between the tip member 22 and the backplate 40) are performed. Typically, a series of assessment impedance measurements are taken throughout the entire procedure and used to position the tip member 22, and monitor ice ball 82 formation, growth and stability. As the ice ball 82 grows, the measured impedance between the tip member 22 and the reference electrode gradually increases (illustrated by the increase in impedance from point C to point D in FIG. 7). Specifically, the conductance is proportional to the surface area of the tip member 22 that is not in contact with the ice ball 82. For example, FIG. 5 shows the ice ball 82 after about half of the surface of the tip member 22 is covered with ice. Accordingly, with half of the surface of the tip member 22 covered, a current will be measured (between the tip member 22 and the backplate 40) that is about half of the reference current (i.e. the current measured when the tip member 22 is immersed in the bloodstream).

Figure 7:
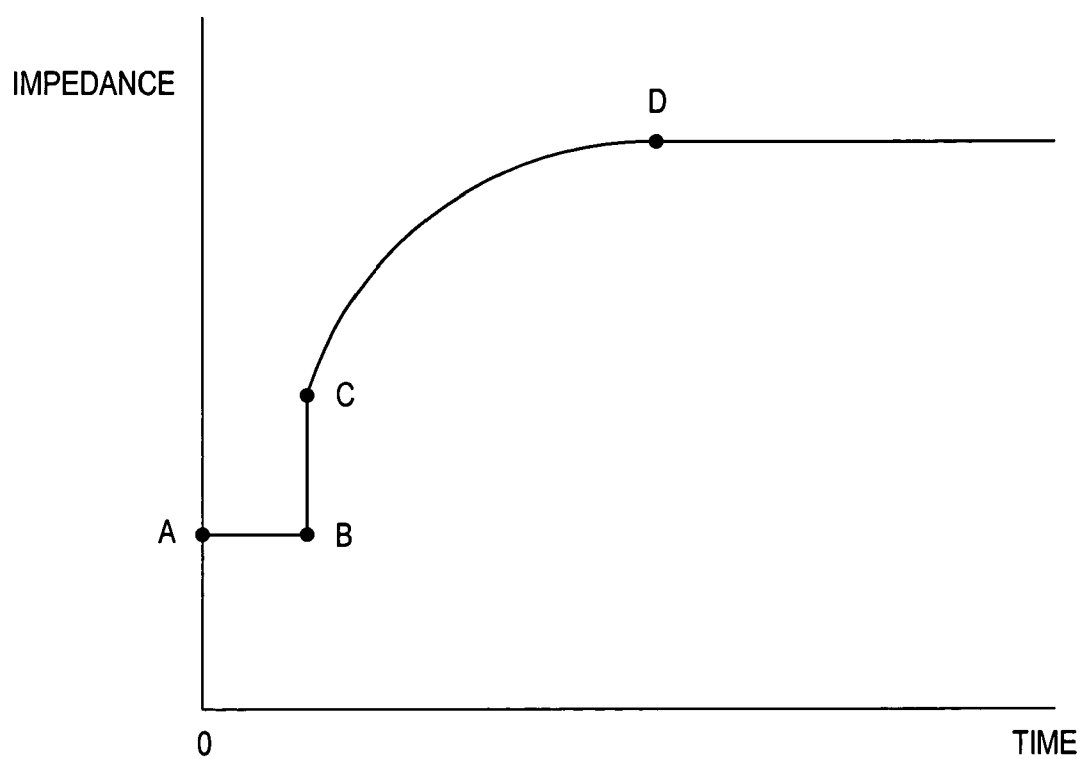
FIG. 7 is an exemplary plot of impedance versus time for the cryoablation procedure illustrated by FIGS. 4–6.

FIG. 6 shows the tip member 22 after it has been covered with ice (illustrated by point D in FIG. 7). At this point, the size of the ice ball 82 stabilizes and the current flow between the tip member 22 and the backplate 40 reduces to almost zero. As shown in FIG. 7, the measured impedance stabilizes and does not significantly change after the tip member 22 has been covered with ice. In a typical procedure, the impedance is monitored until the entire tip member 22 is covered with ice, and thereafter, cooling is controlled to maintain the ice ball 82 for a predetermined time period (e.g. 5 minutes) to effectively cryoablate the target tissue 80.

After the target tissue 80 has been cryoablated, the tip member 22 can be warmed and removed from the patient 12. For example, the tip member 22 can passively absorb ambient heat at the treatment site to warm the tip member 22. It will be appreciated, however, that the tip member 22 can also be warmed by any other devices or methods known to those skilled in the pertinent art.

While the particular System And Method For Assessing Ice Ball Formation During A Cryoablation Procedure as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A method for assessing an ice ball formation during the cryoablation of a target tissue in the vasculature of a patient, said method comprising the steps of:
   providing a cryocatheter having a cryotip wherein said cryotip includes an expansion chamber;
   contacting said patient with a reference electrode;
   positioning said cryotip proximate said target tissue;
   measuring a first impedance between said cryotip and said reference electrode;
   cooling said cryotip by expanding a refrigerant in said expansion chamber; measuring a second impedance between said cryotip and said reference electrode after said cooling step;
   determining a ratio of said first impedance to said second impedance to assess the formation of an ice ball and an extent of the cryoablation of target tissue; and
   expanding said refrigerant in said expansion chamber until a ratio of two measured impedances is substantially zero.

2. A method as recited in claim 1 wherein said first and second impedance are measured using a signal having a frequency of approximately 20 khz.

3. A method as recited in claim 2 wherein said signal has an RMS voltage of approximately 0.5 V.

4. A method as recited in claim 1 wherein said first and second impedance are measured using a signal and said signal is produced by:
   generating a square wave;
   converting said square wave to a sine wave using a four pole, low pass, active filter; and
   rectifying said sine wave using a plurality of analog switches driven by a 20 khz signal that is phase shifted relative to said sine wave by approximately 90 degrees.

5. A method as recited in claim 1 wherein said refrigerant is expanded in said expansion chamber after said ratio of two measured impedances is substantially zero.

6. A method as recited in claim 1 wherein said reference electrode is a backplate.

7. A method for assessing an ice ball formation during the cryoablation of a target tissue of a patient, said method comprising the steps of:
   contacting the patient with a reference electrode;

providing a cryocatheter having a cryotip wherein said cryotip includes an expansion chamber;

cooling said cryotip by expanding a refrigerant in said expansion chamber to create an ice ball and cryoablate said target tissue;

generating a measurement signal having a frequency in the range of 15 to 25 khz and an RMS voltage of less than 1.0V;

using said measurement signal to measure a current between said cryotip and said reference electrode to assess the formation of said ice ball; and expanding said refrigerant in said expansion chamber until said current is substantially zero.

8. A method as recited in claim 7 wherein said measurement signal is generated by:

producing a square wave;

converting said square wave to a sine wave using a four pole, low pass, active filter; and rectifying said sine wave using a plurality of analog switches driven by a signal that is phase shifted relative to said sine wave by approximately 90 degrees.

9. A method as recited in claim 7 wherein said refrigerant is expanded in said expansion chamber after said current is substantially zero.

10. A method as recited in claim 7 wherein said reference electrode is a backplate.

11. A system for assessing ice ball formation during the cryoablation of a target tissue of a patient, said system comprising:

a reference electrode for contacting said patient;

a cryocatheter having a cryotip wherein said cryotip includes an expansion chamber;

a means for positioning said cryotip proximate said target tissue;

a means for cooling said cryotip by expanding a refrigerant in said expansion chamber to create an ice ball and cryoablate said target tissue; and an electronic means connected to said cryotip and said reference electrode to measure an impedance therebetween to assess formation of said ice ball and to allow for expanding said refrigerant in said expansion chamber until a ratio of two measured impedances is substantially zero.

12. A system as recited in claim 11 wherein said electronic means measures said impedance using a signal having a frequency of approximately 20 khz.

13. A system as recited in claim 12 wherein said signal has an RMS voltage of approximately 0.5V.

14. A system as recited in claim 11 wherein said electronic means comprises:

a means for generating a square wave;

a four pole, low pass, active filter for converting said square wave to a sine wave; and a plurality of analog switches, said switches for rectifying said sine wave driven by a 20 khz signal that is phase shifted relative to said sine wave by approximately 90 degrees.

15. A system as recited in claim 11 wherein said cryotip is formed with an expansion chamber and said means for cooling said cryotip includes a means for expanding a refrigerant in said expansion chamber.

16. A system as recited in claim 11 wherein said reference electrode is a backplate.

17. A method for assessing contact between a cryotip of a cryocatheter and a target tissue in the vasculature of a patient, said method comprising the steps of:

contacting said patient with a reference electrode;

positioning said cryotip proximate said target tissue;

measuring a first impedance between said cryotip and said reference electrode;

moving said cryotip relative to said target tissue;

measuring a second impedance between said cryotip and said reference electrode after said moving step; and determining a ratio of said first impedance to said second impedance wherein said first and second impedance are measured using a signal having a frequency of approximately 20 khz and an RMS voltage of approximately 0.5V and said signal is produced by generating a square wave, then converting said square wave to a sine wave using a four pole, low pass, active filter, and rectifying said sine wave using a plurality of analog switches driven by a 20 khz signal that is phase shifted relative to said sine wave by approximately 90 decrees to assess contact between said cryotip and said target tissue.

* * * * *